United States Patent
Ren et al.

(10) Patent No.: US 10,316,058 B2
(45) Date of Patent: Jun. 11, 2019

(54) METHOD FOR MOLECULAR EXTRACTION IN LIVE CELLS

(71) Applicants: Zhifeng Ren, Houston, TX (US); Dong Cai, Houston, TX (US); Zhen Yang, Houston, TX (US); University of Houston System, Houston, TX (US)

(72) Inventors: Zhifeng Ren, Houston, TX (US); Dong Cai, Houston, TX (US); Zhen Yang, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 213 days.

(21) Appl. No.: 15/501,796

(22) PCT Filed: Aug. 4, 2015

(86) PCT No.: PCT/US2015/043546
§ 371 (c)(1),
(2) Date: Feb. 3, 2017

(87) PCT Pub. No.: WO2016/022524
PCT Pub. Date: Feb. 11, 2016

(65) Prior Publication Data
US 2017/0233435 A1    Aug. 17, 2017

Related U.S. Application Data

(60) Provisional application No. 62/032,996, filed on Aug. 4, 2014.

(51) Int. Cl.
*C07K 1/14*    (2006.01)
*C12N 13/00*    (2006.01)
*G01N 33/543*    (2006.01)

(52) U.S. Cl.
CPC ............... *C07K 1/14* (2013.01); *C12N 13/00* (2013.01); *G01N 33/54326* (2013.01)

(58) Field of Classification Search
None
See application file for complete search history.

(56) References Cited

U.S. PATENT DOCUMENTS

2007/0231908 A1    10/2007    Cai
2011/0279944 A1    11/2011    Seeney

OTHER PUBLICATIONS

Initial Publication with International Search Report for PCT/US2015/043546 dated Feb. 11, 2016.
Yang, Zhen et al., Molecular extraction in single live cells by sneaking in and out magnetic nanomaterials, Proceedings of the National Academy of Sciences, Jul. 29, 2014, vol. 111, No. 30, pp. 10966-10971 (6 pages).
Cai, Dong et al., Highly efficient molecular delivery into mammalian cells using carbon nanotube spearing, Nature Methods, 2005, vol. 2, No. 6,—Abstract (1 page.
Melechko, Anatoli V. et al., Synthesis of vertically aligned carbon nanofibres for interfacing with live systems, Journal of Physics D: Applied Physics, 2009, vol. 42, No. 19, Issue No. 193001—abstract (1 page).
Deng et al., "Layer-by-Layer Nanoparticles for Systemic Codelivery of an Anticancer Drug and siRNA for Potential Triple-Negative Breast Cancer Treatment," vol. 7, No. 11, pp. 9571-9584, 2013, ACSNANO.
Marx et al., "Electropolymerized Tyrosine-Based Thin Films: Selective Cell Binding via Peptide Recognition to Novel Electropolymerized Biomimetic Tyrosine RGDY Films," Anal. Biochem. 384 (2009) pp. 86-95.
Marx et al., "Electropolymerized Films Formed from the Amphiphilic Decyl Esters of D- and L-Tyrosine Compared to L-Tyrosine Using the Electrochemical Quartz Crystal Microbalance," Biomacromolecules, vol. 6, No. 3, 2005, pp. 1698-1706.
Kostarelos et al., "Cellular Uptake of Functionalized Carbon Nanotubes is Independent of Functional Group and Cell Type," Nature Nanotechnology, vol. 2, Feb. 2007, pp. 108-113.
Yang et al., "Molecular Extraction in Single Live Cells by Sneaking in and out Magnetic Nanomaterials," PNAS, Jul. 29, 2014, vol. 111, No. 30, pp. 10966-10971.
Ren et al., "Synthesis of Large Arrays of Well-Aligned Carbon Nanotubes on Glass," Science, vol. 282, Nov. 6, 1998, pp. 1105-1107.

*Primary Examiner* — Anand U Desai
(74) *Attorney, Agent, or Firm* — Conley Rose, P.C.

(57) ABSTRACT

A method of extracting biomolecules from live cells comprising: introducing a plurality of magnetized carbon nanotubes (MCNTs) into a live cell, wherein the MCNTs penetrate the cell membrane under a magnetic force; spearing the MCNTs through the cell under the magnetic force, wherein a biomolecule attaches to at least a portion of the MCNTs to form a biomolecule loaded MCNT; removing at least a portion of the biomolecule loaded MCNTs from the cell under the magnetic force; and collecting at least a portion of the biomolecule loaded MCNTs.

15 Claims, 18 Drawing Sheets

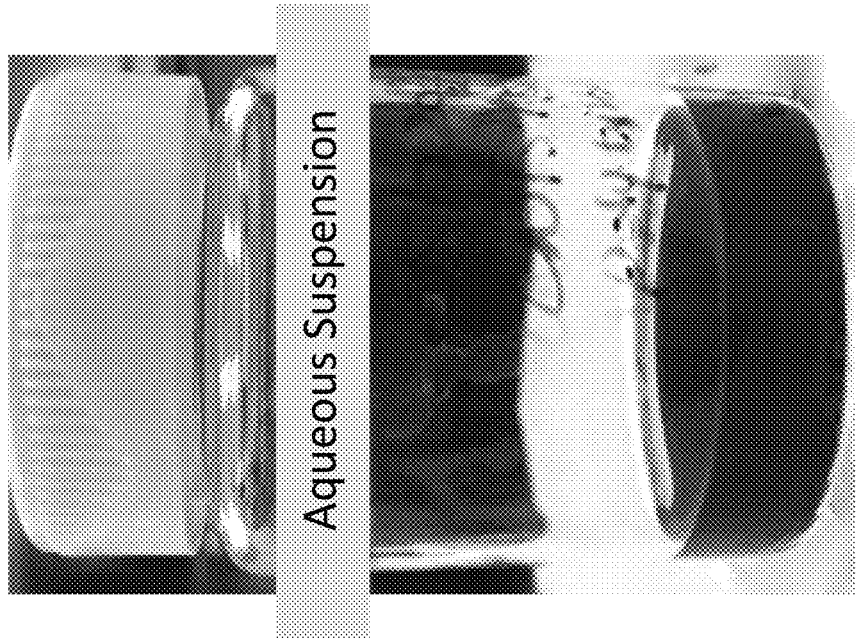

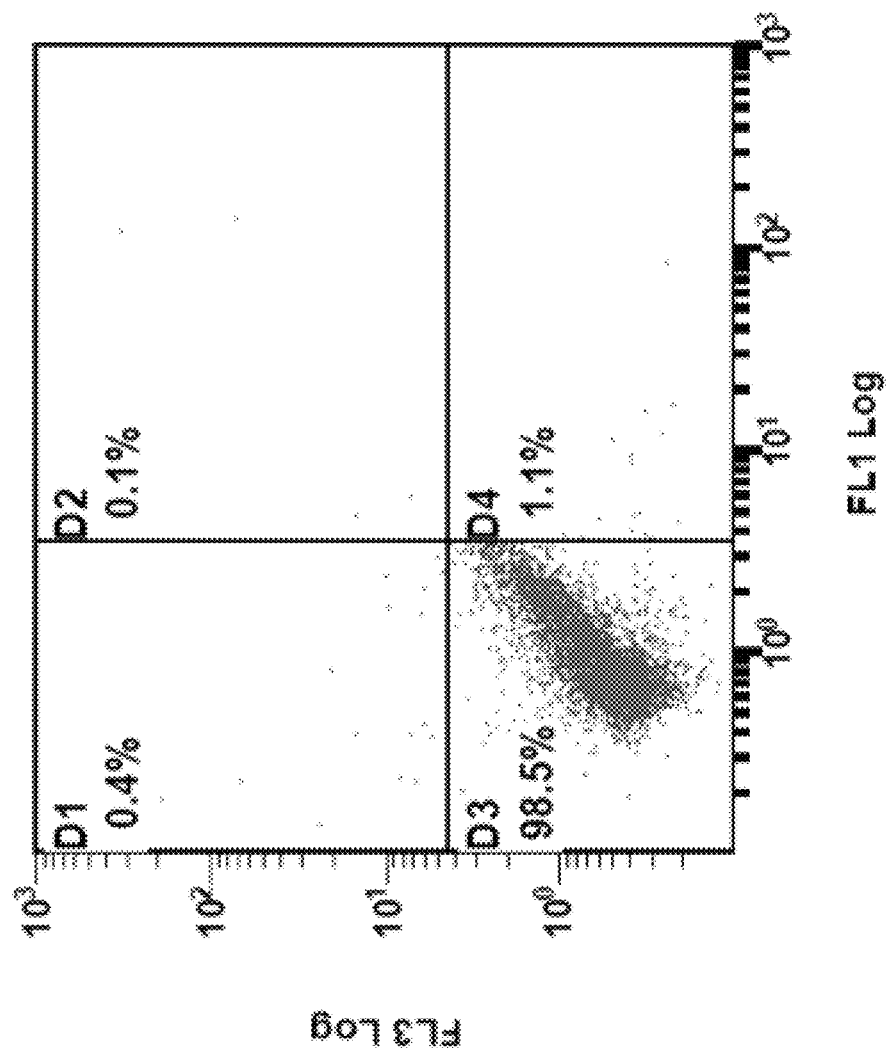

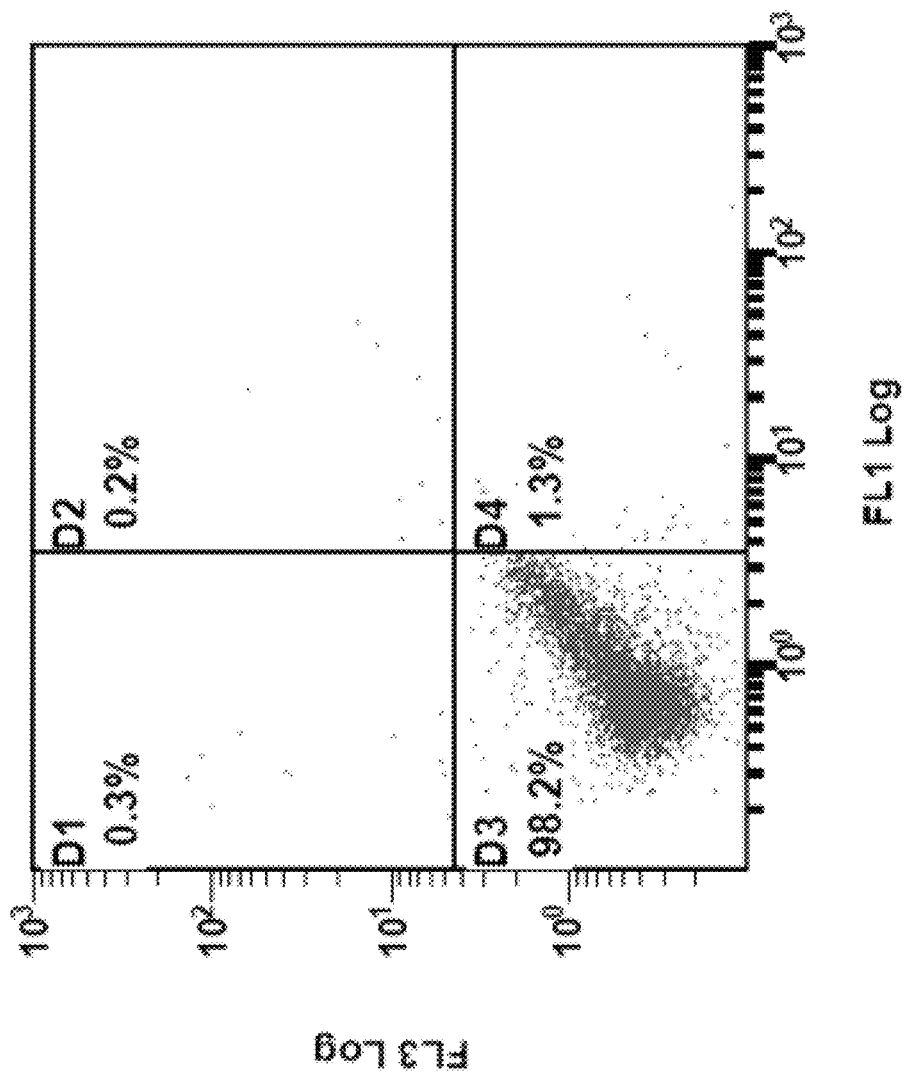

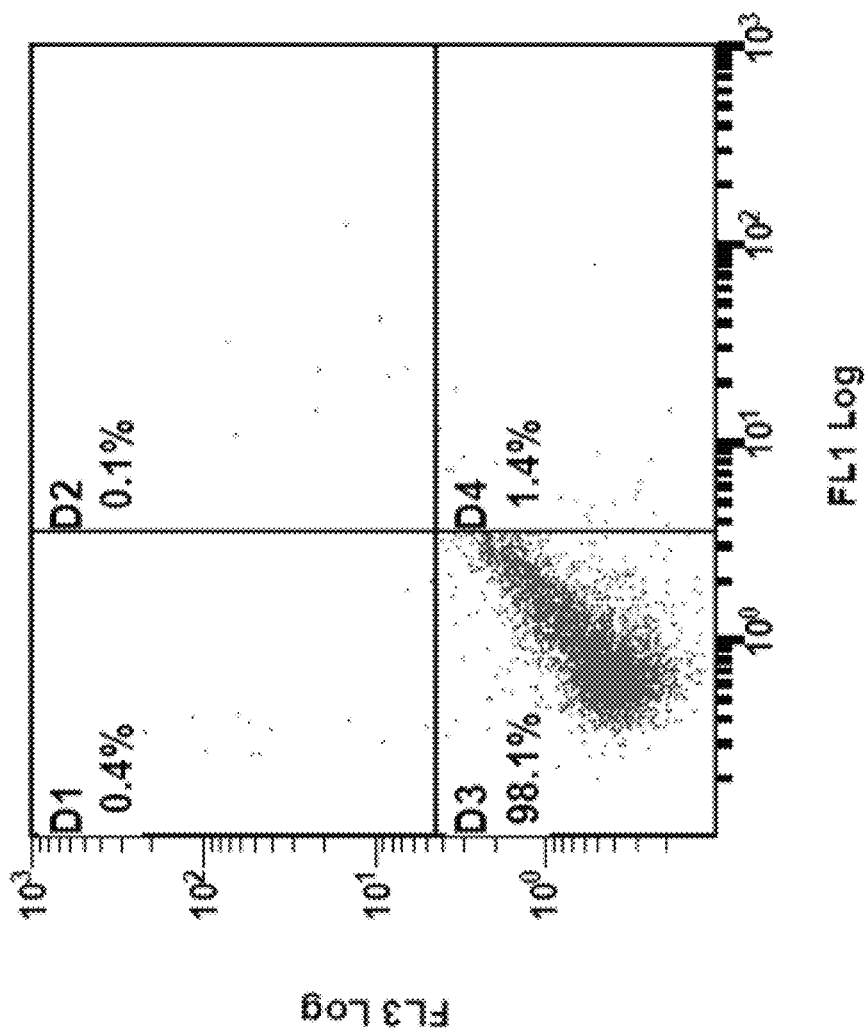

US 10,316,058 B2

METHOD FOR MOLECULAR EXTRACTION IN LIVE CELLS

CROSS-REFERENCE TO RELATED APPLICATIONS

This US National Stage Application under 35 U.S.C. § 371 claims priority to International Patent Application No. PCT/US2015/043546 filed Aug. 4, 2015, which claims priority from U.S. Provisional Application 62/032,996 filed on Aug. 4, 2014, both of which are incorporated herein in their entirety by this reference.

STATEMENT REGARDING SPONSORED RESEARCH

The invention described and claimed herein was made in part utilizing funds supplied by US Air Force Office of Scientific Research Grant FA9550-09-1-0656, the T. L. L. Temple Foundation, the John J. and Rebecca Moores Endowment, and the State of Texas through the Texas Center for Superconductivity at the University of Houston.

TECHNICAL FIELD

This disclosure relates to methods of molecular extraction in live cells. More specifically, it relates to methods of using magnetic nanomaterials to extract biomolecules from live cells.

BACKGROUND

Identification, quantification, and characterization of intracellular molecules in live cells are essential to dissect the intracellular pathways and networks to understand physiology and pathogenesis at the cellular level (1-5). Cell lysis by disrupting the cellular membrane to release intracellular molecules is a conventional laboratory technique to prepare samples for analysis of genes, proteins, and metabolites (6-8). Due to the termination of cell lives that results from this procedure, the progressive information is lost. The inconsistency of molecular background in the cell preparations for samples taken at different points in time largely compromises the study of cell differentiation, pathogenesis development, and therapeutic effectiveness. The extraction of intracellular molecules without killing cells so that repetitive sampling can be conducted at successive points in time is becoming an imperative and urgent mission.

Additionally, cellular heterogeneity is frequently observed, particularly in cancer cells (9). However, the traditional biochemical analysis only provides the average of the cellular information with an ensemble of molecules from a large quantity of cells. Single-cell analysis is essential to obtain the physiological and pathological characteristics with respect to the genetic, proteomic, spatial, and temporal diversity of cells in cell biology and cancer research (10-12). Although microfluidics and lab-on-chip have been widely applied to single-cell manipulation via cell trapping, isolation, and sorting, the analyte extraction still relies on complete lysis (13, 14).

Physical penetration of the cell membrane has exhibited low invasiveness in the extraction or release of intracellular molecules (15, 16). Nanoneedle and optoporation were utilized for subcellular disruption and manipulation in living cells, but special and sophisticated setups are often required to wage the high spatial resolution and precise manipulation (17-20). Electroporation was also demonstrated to release intracellular proteins without loss of cell viability (21). However, the efficiency can be limited due to its dependence on diffusion to release the molecules. To date, the efficient extraction of molecules from live cells at the single cell level remains a significant challenge in biotechnology.

Extraction of intracellular molecules is crucial to the study of cellular signaling pathways. Disruption of the cellular membrane remains the established method to release the intracellular contents, which inevitably terminates the time course of biological processes. Also, conventional lab extractions mostly employ bulky materials that ignore the heterogeneity of each cell.

Current technical barriers in molecular sampling compromise the biomedical research regarding the diversity of cellular background. Usually hundreds and thousands of cells are lysed to release their contents. As such, the differences among individual cells are averaged out. The progressive cellular information can only be obtained by analysis of cells terminated at sequential points in time, or by using external fluorescent and chemical labels that may interfere with pathways. As such, there exists a need for improved methods of interrogating cellular signaling pathways.

BRIEF DESCRIPTION OF THE DRAWINGS

For a more complete understanding of the present disclosure, reference will now be made to the accompanying drawings/figures in which.

SUMMARY OF THE DISCLOSURE

Figure 1A:
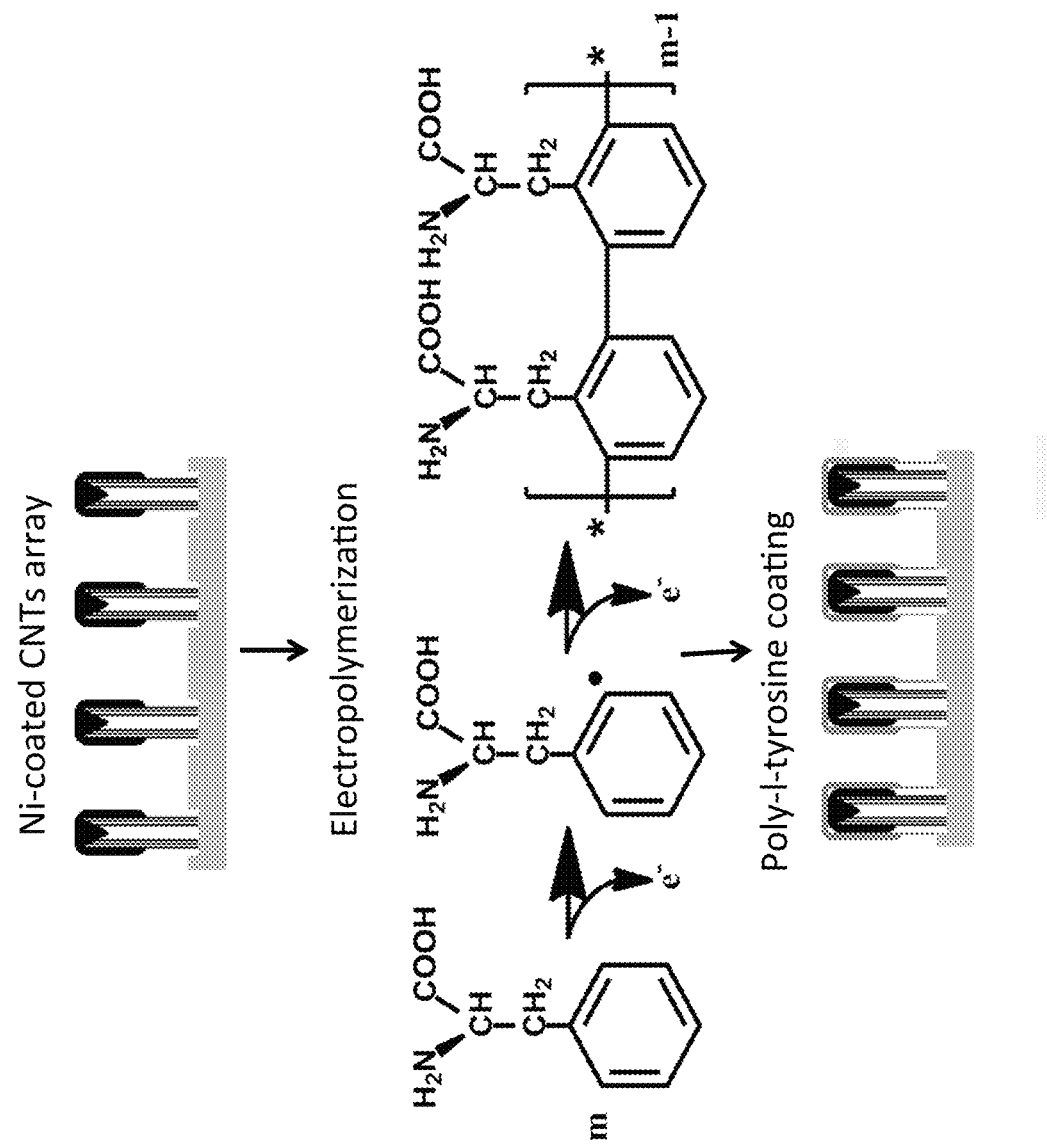
FIG. 1 illustrates surface modification and characterization of MCNTs. (A) Schematic illustration of surface modification of MCNTs: Ni-coated CNTs array by e-beam evaporation of Ni on aligned CNTs array, and poly-$_L$-tyrosine coating by electropolymerization. (B) Recording of cyclic voltammetry (CV) for electropolymerization of $_L$-tyrosine on CNTs with CNTs and Ag/AgCl as the working and reference electrodes, respectively. (C) Deposition charge (Q) by integration of each cycle of CV versus the cycles. (D) SEM image of Ni-coated CNTs. (E) TEM images of Ni-coated CNTs with surface modified by poly-$_L$-tyrosine coating, as indicated by the red arrow; inset: a low magnification image. (F) Magnetization measurement of Ni-coated CNTs. (G) Aqueous suspension of the magnetized MCNTs.

Disclosed herein is a method of extracting biomolecules from live cells comprising introducing a plurality of magnetized carbon nanotubes into a live cell, wherein the magnetized carbon nanotubes (MCNTs) penetrate the cell membrane under a magnetic force; spearing the MCNTs through the cell under the magnetic force, wherein a biomolecule attaches to the MCNTs, or attaches to at least a portion of the MCNTs to form a biomolecule loaded MCNT; removing at least a portion of the biomolecule loaded MCNTs from the cell under the magnetic force; and collecting at least a portion of the biomolecule loaded MCNTs.

Further disclosed herein is a method of preparing magnetized carbon nanotubes (MCNTs) comprising growing carbon nanotubes; coating the carbon nanotubes with a magnetic metal to yield MCNTs, wherein the magnetic metal comprises nickel; and coating the MCNTs with an outer polymeric layer, wherein the outer polymeric layer is hydrophilic and biocompatible.

Also disclosed herein is a method of extracting biomolecules from live cells comprising introducing a plurality of magnetized nanostructures (mNSs) into a bioentity, wherein the mNSs penetrate the cell membrane under a magnetic force; spearing the mNSs through the bioentity under the magnetic force, wherein biomolecules attach to at least a portion of the mNS to form a biomolecule loaded mNSs; removing at least a portion of the biomolecule loaded mNSs from the bioentity under the magnetic force; and collecting at least a portion of the biomolecule loaded mNSs.

The foregoing has outlined rather broadly certain of the features of the exemplary embodiments of the present invention in order that the detailed description that follows may be better understood. It should be appreciated by those skilled in the art that the conception and the specific embodiments disclosed may be readily utilized as a basis for modifying or designing other methods and structures for carrying out the same purposes of the invention that is claimed below.

DETAILED DESCRIPTION OF DISCLOSED EXEMPLARY EMBODIMENTS

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

The following discussion is directed to various exemplary embodiments of the disclosure. One skilled in the art will understand that the following description has broad application, and the discussion of any embodiment is meant only to be exemplary of that embodiment, and that the scope of this disclosure, including the claims set out below, is not limited to that embodiment.

The drawing figures are not necessarily to scale. Certain features and components herein may be shown exaggerated in scale or in somewhat schematic form and some details of conventional elements may be omitted in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component or device couples to a second, that connection may be through a direct engagement between the two components or devices, or through an indirect connection that is made via other intermediate devices and connections. As used herein, the term "about," when used in conjunction with a percentage or other numerical amount, means plus or minus 10% of that percentage or other numerical amount. For example, the term "about 80%," would encompass 80% plus or minus 8%.

Overview

Disclosed herein are embodiments of methods of extracting biomolecules from live cells by using magnetized carbon nanotubes (MCNTs). While the current disclosure will be discussed in detail in the context of methods using MCNTs for extracting biomolecules from live cells, it should be understood that other magnetic nanomaterials, such as for example magnetic nanoparticles, magnetic nanorods, etc., could be used for extracting biomolecules from live cells. The magnetic nanomaterials can comprise any magnetic nanomaterials compatible with the disclosed methods and materials. The current disclosure presents a novel, real-time and single-cell approach to investigate cellular biology, signal messengers, and therapeutic effects with nanomaterials (e.g., MCNTs).

For purposes of this disclosure, a biomolecule can be defined as any molecule that is produced by a living organism, including large macromolecules such as proteins, polysaccharides, lipids, and nucleic acids, as well as small molecules such as primary metabolites, secondary metabolites, and natural products. In an embodiment, the biomolecule can comprise intracellular molecules, intracellular proteins, analytes, signaling molecules, and the like, or combinations thereof.

Magnetized Carbon Nanotubes (MCNTs)

In an embodiment, nanomaterials can be used for extracting biomolecules from live cells, wherein the nanomaterials comprise biocompatible magnetic nanostructures, such as for example MCNTs. In such embodiment, MCNTs can enter into and exit out of cell bodies under a magnetic force.

In an embodiment, MCNTs can comprise carbon nanotubes (CNTs), a magnetic metal and an outer polymeric layer. In an embodiment, the magnetic metal can comprise magnetic particles and a magnetic metal layer. In an embodiment, the magnetic metal can comprise nickel (Ni), superparamagnetic materials, and the like, or combinations thereof.

In an embodiment, the CNTs have a rod shape or cylindrical geometry. In such embodiment, the CNTs can be characterized by having two ends, which correspond to the ends of the rod or cylinder. Further, in such embodiment, the magnetic metal can coat only one end of the MCNTs. Coating only one end of the CNTs with a magnetic material (e.g., magnetic metal) ensures that the resulting MCNTs could be oriented in the magnetic field, and could consequently be "speared" in the desired direction. As used herein, the terms "spear" or "spearing," and "nanospear" or "nanospearing," are used interchangeably and all these related terms refer to a directed movement of a magnetized nanostructure (mNS) within and/or through a bioentity (e.g., a single cell, a clump of cells, a piece of live tissue, etc.). Nonlimiting examples of mNS include MCNT, nanotube, nanoparticle, nanorod, nanowire, nanohorn, nanostar, nanovesicle, nanocapsule that are made of inorganic, organic, polymeric, metallic, non-metallic, oxide, alloy, or composite materials, and the like, or combinations thereof.

In an embodiment, the MCNTs can be characterized by a MCNT length of from about 0.5 mm to about 5 mm, alternatively from about 1 mm to about 3 mm, or alternatively from about 1 mm to about 2 mm.

In an embodiment, the MCNTs can be characterized by a MCNT diameter of from about 50 nm to about 300 nm, alternatively from about 75 nm to about 200 nm, or alternatively from about 75 nm to about 125 nm.

In an embodiment, a method of preparing MCNTs can comprise growing carbon nanotubes; coating the carbon nanotubes with a magnetic metal to yield MCNTs, wherein the magnetic metal can comprise nickel; and coating the MCNTs with an outer polymeric layer, wherein the outer polymeric layer can be hydrophilic and biocompatible.

In an embodiment, the CNTs can be grown by using any suitable methodology. In an embodiment, the CNTs can be grown by using a plasma-enhanced chemical vapor deposition system, as described in more detail in Science 1998, 282 (5391): 1105-1107 (27), which is incorporated by reference herein in its entirety. The growth of the CNTs can result in straight-aligned CNTs with magnetic nickel (Ni) particles enclosed at the tips, which make the CNTs magnetically drivable. In an embodiment, a layer of a magnetic metal (e.g., Ni) can be deposited along the surface of individual CNTs by using any suitable methodology, such as for example e-beam evaporation. In an embodiment, the layer of magnetic metal can enhance the magnetization, thereby leading to an enhanced magnetic force, wherein such magnetic force may be required for cell penetration. The magnetic metal can exacerbate toxicity and hydrophobicity of the MCNTs for biological applications.

In an embodiment, the magnetic metal layer can be characterized by a magnetic metal layer thickness of from about 5 nm to about 50 nm, alternatively from about 10 nm to about 30 nm, or alternatively from about 15 nm to about 25 nm.

In an embodiment, the MCNTs (e.g., MCNTs array) can be further coated with the outer polymeric layer by using any suitable methodology, such as for example electropolymerization, thereby reducing the toxicity of metal (e.g., Ni)-coated CNTs. In such embodiment, the outer polymeric layer can comprise poly-L-tyrosine. In an embodiment, the outer polymeric layer can be hydrophilic, thereby rendering the MCNTs hydrophilic. In an embodiment, the outer polymeric layer can be biocompatible, thereby rendering the MCNTs biocompatible.

In an embodiment, the outer polymeric layer can be characterized by an outer polymeric layer thickness of from about 1 nm to about 50 nm, alternatively from about 2 nm to about 25 nm, or alternatively from about 5 nm to about 15 nm.

In an embodiment, the MCNTs (e.g., MCNTs array) can be connected to an electrochemistry system to conduct electropolymerization of a monomer (e.g., $_L$-tyrosine) on the surfaces of the MCNTs, as illustrated in FIG. 1A. It has been previously shown that electropolymerization of $_L$-tyrosine can be a feasible way to create a hydrophilic and biocompatible film that is suitable in diverse biological applications, as described in more detail in Biomacromolecules 2005, 6(3):1698-1706 and Anal Biochem 2009, 384(1):86-95 (28, 29), each of which is incorporated by reference herein in its entirety. In an embodiment, elctropolimerization of $_L$-tyrosine into poly-$_L$-tyrosine can comprise cyclic voltammetry.

Molecular Extraction

In an embodiment, nanomaterials (e.g., MCNTs) can be introduced to a live cell, wherein the nanomaterials can enter into the cell by being transported across cell membranes by native biological processes or with negligible invasiveness, as described in more detail in Nanotechnol 2007, 2(2):108-113 and ACS Nano 2013, 7(11): 9571-9584 (22, 23), each of which is incorporated by reference herein in its entirety.

In an embodiment, highly efficient molecular delivery into cells can be achieved by carbon nanotube spearing as described in more detail in Nat Methods 2005, 2(6): 449-454 (24). It has been previously demonstrated that MCNTs can be driven by a magnetic force to spear into cells and deliver molecular payloads. Such spearing method has demonstrated remarkable biocompatibility regarding cell viability, cell growth, cell cycle, DNA synthesis, cellular stimulation, and Akt and MAP kinase activities, as described in more detail in Nanotechnology 2007, 18(36): 365101 and Nanotechnology 2008, 19(34): 1-10 (25, 26). In an embodiment, the MCNTs can penetrate through the cells without detectable perturbations. In such embodiment, MCNTs can be used to extract molecules from live cells. In an embodiment, MCNTs can be used to transport intracellular molecules out of cells by magnetically driving the MCNTs through cells. A recent study of interaction between a one-dimensional nanomaterial and a cell membrane revealed a near-perpendicular entry mode and near-parallel adhering mode (32).

In an embodiment, the live cell can retain integrity of the cell membrane and cytoskeleton upon being subjected to MCNT based molecular extraction. In an embodiment, the viability of the live cells can be decreased by less than about 5%, alternatively by less than about 4%, or alternatively by less than about 3%, when compared to live cells under similar conditions lacking the MCNTs. In some embodiments, integrity is the robustness of the cell membrane, completeness of the cell membrane, wherein the cell membrane does not rupture.

In an embodiment, biomolecules can be extracted from the same single live cell at different time points by using MCNT based molecular extraction. In such embodiment, owing to the fact that the molecular extraction method of the present disclosure does not alter the viability of the live cell, the same single live cell can be subjected to multiple rounds of MCNT based molecular extraction, at various time points.

Figure 2:
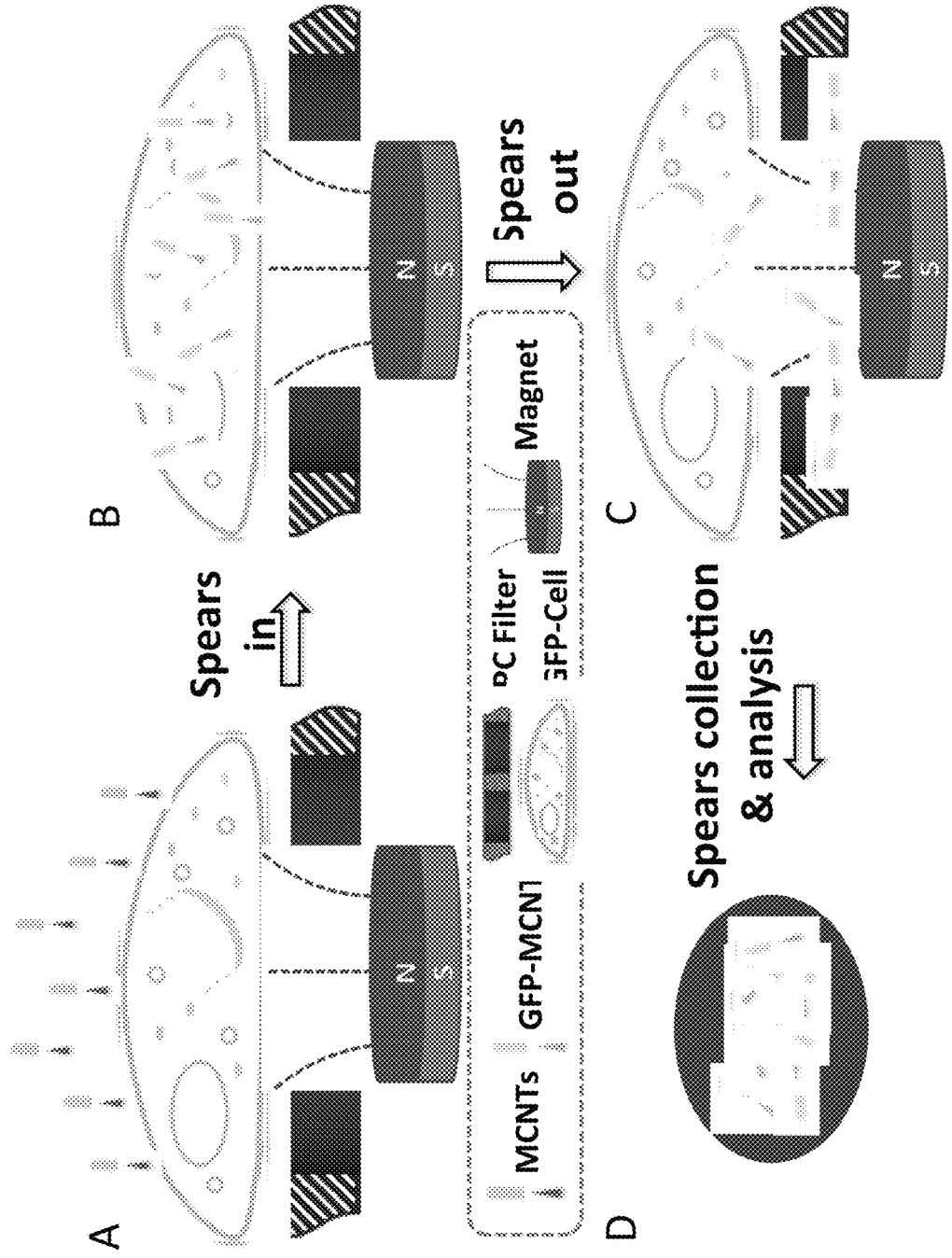
FIG. 2 illustrates molecular extraction by spearing into and out of cells: (A) An external magnetic field drives magnetized carbon nanotubes (MCNTs) toward a cell cultured on a polycarbonate filter. To indicate the molecular extraction, the cell is transfected for green fluorescent protein (GFP) overexpression beforehand. (B) MCNTs spear into the cell under the magnetic force. (C) MCNTs spear through and out of the cell and have GFP extracted. The GFP-carrying spears are collected within the pores of the polycarbonate filter. (D) At individual pores, the GFP representing the intracellular signal molecules can be used for analysis.

FIG. 2 displays a schematic of the method of extracting biomolecules from live cells comprising introducing a plurality of magnetized carbon nanotubes into a live cell. In an embodiment, the cells can be cultured, such as for example on a polycarbonate filter. The cells can be transfected, such as for example with a green fluorescent protein (GFP)-plasmid, as seen in FIG. 2A.

In an embodiment, the method of extracting biomolecules from live cells can comprise introducing or spearing a plurality of MCNTs into a live cell, wherein the MCNTs can penetrate the cell membrane under a magnetic force. In such embodiment, a magnetic force can be applied from the bottom of cells, so that the MCNTs can first spear into the cells, and then travel through the cells to spear out, as seen in FIG. 2B.

In an embodiment, the method of extracting biomolecules from live cells can comprise spearing the MCNTs through the cell under the magnetic force, wherein a biomolecule attaches to at least a portion of the MCNTs to form a biomolecule loaded MCNT. In such embodiment, the MCNTs can adsorb or absorb biomolecules (e.g., GFP) on their surfaces while traveling through the cellular cytoplasm to form biomolecule loaded MCNTs, as seen in FIG. 2C.

In an embodiment, the method of extracting biomolecules from live cells can comprise removing at least a portion of the biomolecule loaded MCNTs from the cell under the magnetic force. In an embodiment, the method of extracting biomolecules from live cells can comprise collecting at least a portion of the biomolecule loaded MCNTs. In such embodiment, a filter (e.g., track-etched polycarbonate filter) can serve as a nanotubes collector, and the collected nanotubes (e.g., biomolecule loaded MCNTs) with intracellular biomolecules (e.g., GFP) can be ultimately used for cellular analysis (e.g., cellular signaling analysis).

In an embodiment, the method of extracting biomolecules from live cells comprising introducing a plurality of MCNTs into a live cell as disclosed herein advantageously displays improvements in one or more outcomes when compared to a method of extracting biomolecules from live cells utilizing a means other than MCNTs. In an embodiment, nanomaterials (e.g., MCNTs) can enter into and exit out of cells carrying molecules across cell membranes without detectible impact on cell viability or proliferation. In such embodiment, molecular information can be advantageously captured through a label free cellular study to accurately capture the diversity of available metabolic data. In an embodiment, MCNTs have a low level of invasiveness that is confined at nanoscale level, and as such MCNTs do not change cell viability or proliferation. Additional advantages of the method of extracting biomolecules from live cells comprising introducing a plurality of MCNTs into a live cell may be apparent to one of skill in the art viewing this disclosure.

EXAMPLES

The following examples are given as particular exemplary embodiments of the disclosure and to demonstrate the practice thereof. It is understood that the examples are given by way of illustration and are not intended to limit the specification or the claims in any manner.

The experiments presented as examples in the current disclosure have been conducted by using the following methodology.

MCNTs preparation. A straightly aligned CNTs array was obtained by a homemade plasma-enhanced chemical vapor deposition system as previously described (25). 10 nm nickel was deposited as the catalyst and produced CNTs of about 1.5 µm length with 10 min growth. The average diameter of CNT was 100 nm. The CNTs array was then put into an e-beam evaporation system to deposit 20 nm nickel on the surface of the CNTs. The Ni-coated CNTs array was connected into an electrochemical system equipped with three electrodes, i.e. MCNTs as working electrode, Pt wire as counter electrode, and Ag/AgCl as reference electrode. Electrolyte solution was prepared by 3 mM L-tyrosine dissolved in 0.1 M phosphate buffer of pH 6.5 containing 0.4 M NaCl. Electropolymerization of L-tyrosine was then conducted in cyclic voltammetry (CV) with the working electrode potential ramping between 0 and 900 mV versus the reference electrode. Thirty cycles of CV were run to thoroughly coat each MCNT with a poly-L-tyrosine layer. Finally, MCNTs were scraped off from the substrate with 1 hr sonication, and a final aqueous suspension of CNTs was obtained with an estimated concentration of about 1 pM. For the spearing of cells, MCNTs were centrifuged at 10,000 g for 15 min and re-suspended in cell culture medium.

Cell culture, GFP plasmid transfection, and MCNTs spearing. HEK293 cell lines were cultured in DMEM (Life Technologies) containing 10% fetal calf serum and 100 µ/ml penicillin-streptomycin in a humidified atmosphere of 5% CO2, 95% air at 37° C. Substrates for cell culture were sterilized by ethanol and surface-treated by immersion into poly-L-lysine solution (1 mM in sterilized physiological phosphate buffer) overnight to facilitate cell adhesion. For instance, micro grid and polycarbonate filter (8 µm pore size, SterliTech, USA) were first surface-treated as described above and then used as cell culture substrates for SEM imaging and extraction experiments, respectively. For the extraction experiments, a commercial kit (Lipofectamine® LTX with Plus Reagent, Life Technologies) was used to transfect GFP plasmid into HEK293 cells cultured on the polycarbonate filter as the provided protocol indicated. Fluorescent images revealed that ~90% of the transfected cells were GFP-expressed. After GFP expression, 200 µl MCNTs solution of ~1 pM concentration was supplied into a cell culture well, and a Nd—Fe—B permanent magnet was put underneath the well to supply 0.355 T to drive MCNTs spearing through cells in the well. Magnetic force was applied for 10 min and then withdrawn by removal of the magnet from the cell culture well.

Characterization. A JEOL 6330 scanning electron microscope was used to conduct SEM imaging, including the morphology of Ni-coated CNTs and cells that experienced MCNTs spearing. A JEOL 2010 SFX scanning transmission electron microscope was used to observe the morphology of CNTs with Ni-coating and poly-L-tyrosine surface modification. For magnetization properties, lyophilized powder of CNTs was obtained and measured by Quantum Design Magnetometer with the Superconducting Quantum Interference Device with external magnetic field scanned from −1 T to 1 T at 310 K. All of the optical images were obtained by Olympus 1×51 Inverted Fluorescence Microscope equipped with 60× oil objective lens and 40× oil objective lens. To observe the response of the MCNTs to magnetic field, a droplet of aqueous-suspended MCNTs was sealed between two glass slides for microscope images, and a Nd—Fe—B permanent magnet was placed alongside the glass slides to exert pulling force on the MCNTs in planar direction. An image of high magnification was captured to reveal the alignment of MCNTs in magnetic field with 60× oil objective lens. Images of low magnification were captured to reveal the displacement of MCNTs in magnetic field at different time intervals with 40× oil objective lens. For SEM images of cells, cells were fixed with formaldehyde (3.7% diluted with physiological phosphate buffer) reaction for 10 min, and dehydrated by sequentially changing solution with 10%, 30%, 60%, 90%, and 100% ethanol solution (diluted with physiological phosphate buffer). Lastly, the cells on the TEM grid were dried and coated with 5 nm gold, and then imaged using SEM (JEOL 6330F).

Cell viability evaluation. Three groups of cells were cultured to compare the effect of spearing on cell viability. Among those, there were a Mag-Only group with normal cell culture and a Nd—Fe—B permanent magnet underneath, a MCNT-Spearing group with 200 μl MCNTs of about 1 pM spearing cells by 10 min pulling of the Nd—Fe—B magnet and a MCNT-Incubation group with 200 μl MCNTs of about 1 pM supplement into cell culture but no external magnet. For cytometry measurement, one more group was compared, i.e. further incubation of cells for 12 hours after the above spearing stimulus, in addition to the above three groups. Before flow cytometry, cells were collected with 0.25% trypsin. The collected cells were co-stained with 10 μM Annexin V-FITC and propidium iodide (Annexin V-FITC/PI kits purchased from KeyGEN Biotech, China). After 15 min incubation in dark light, cells were launched into cytometry (Beckman FC500) for detection of cell death and cell apoptosis.

Example 1

Figure 1B:
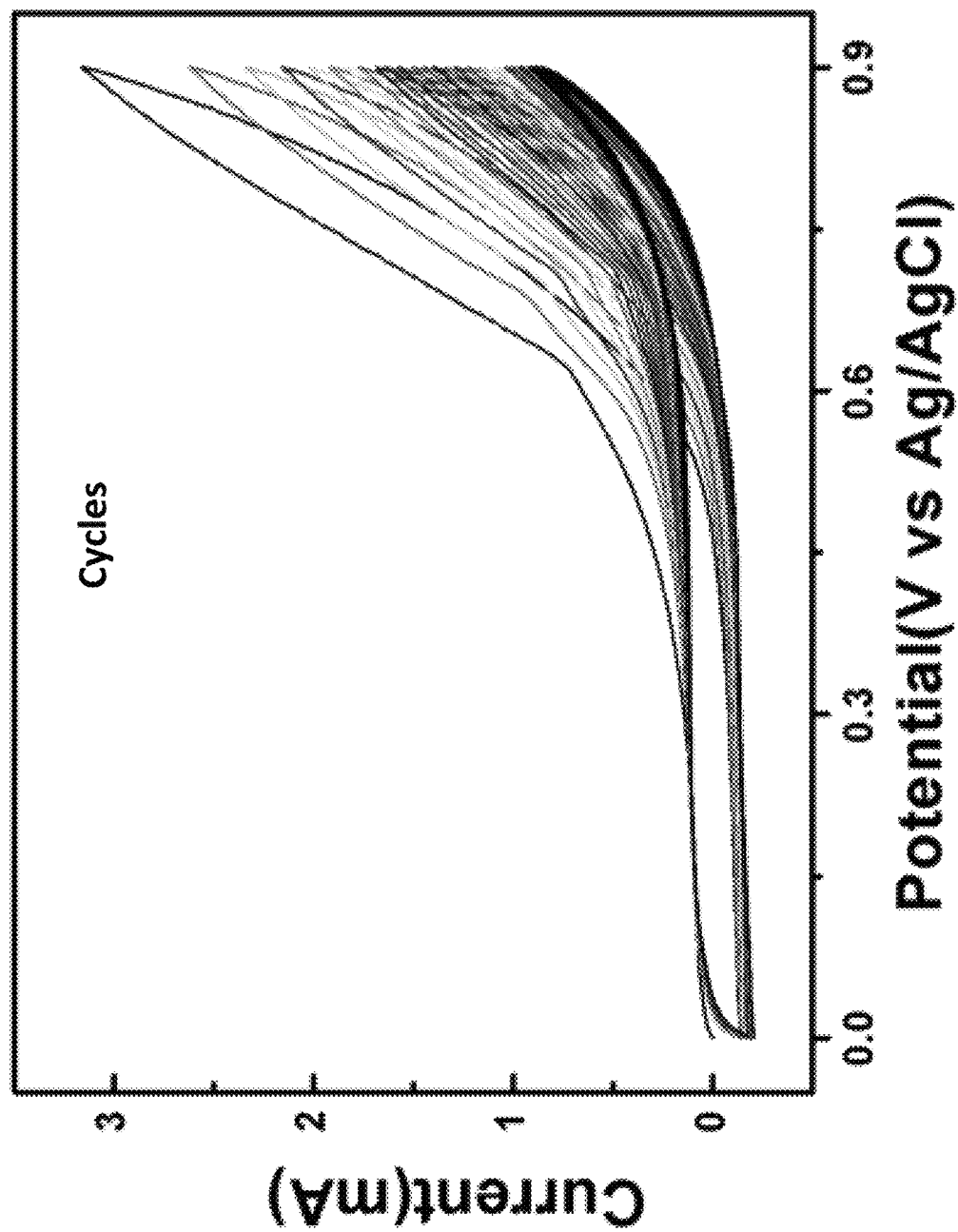
Figure 1C:
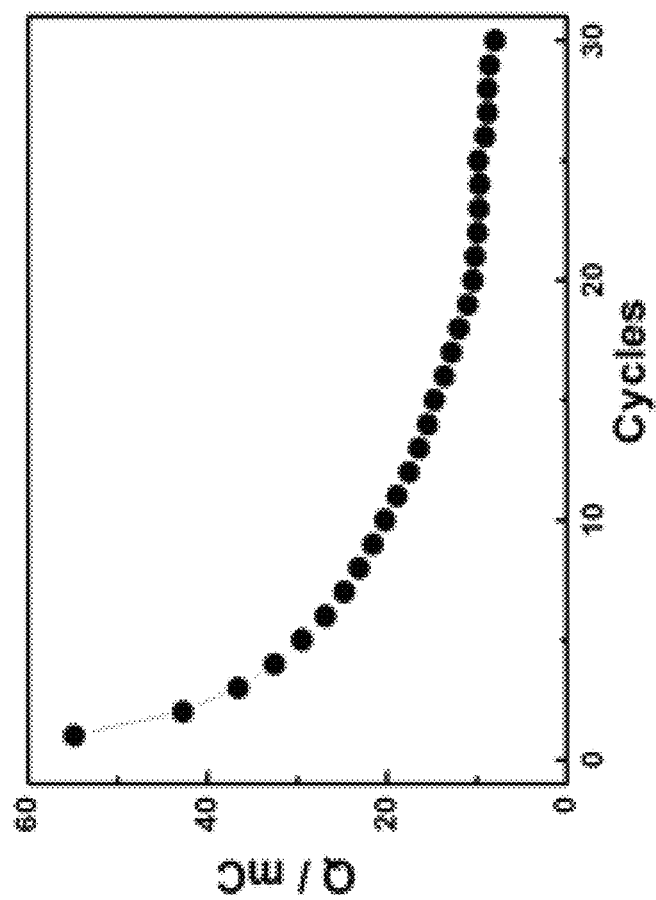
Figure 1D:
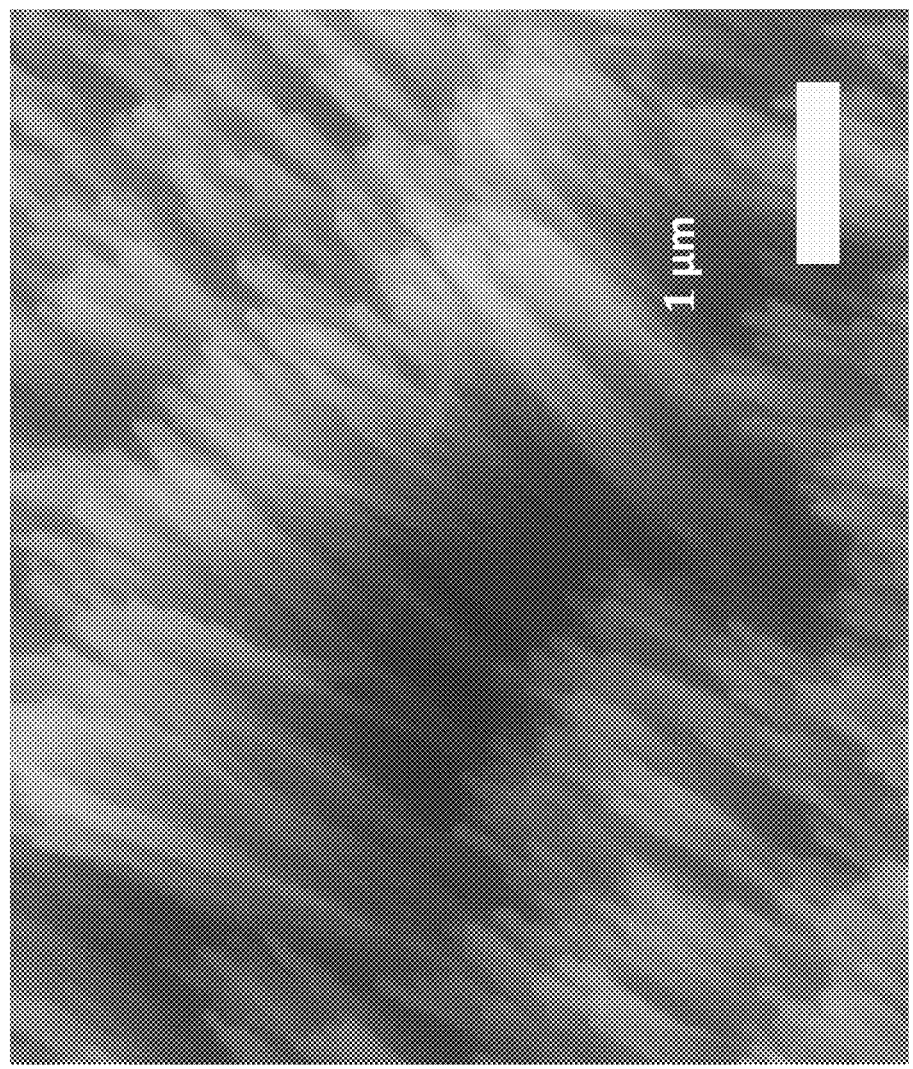
Figure 1E:
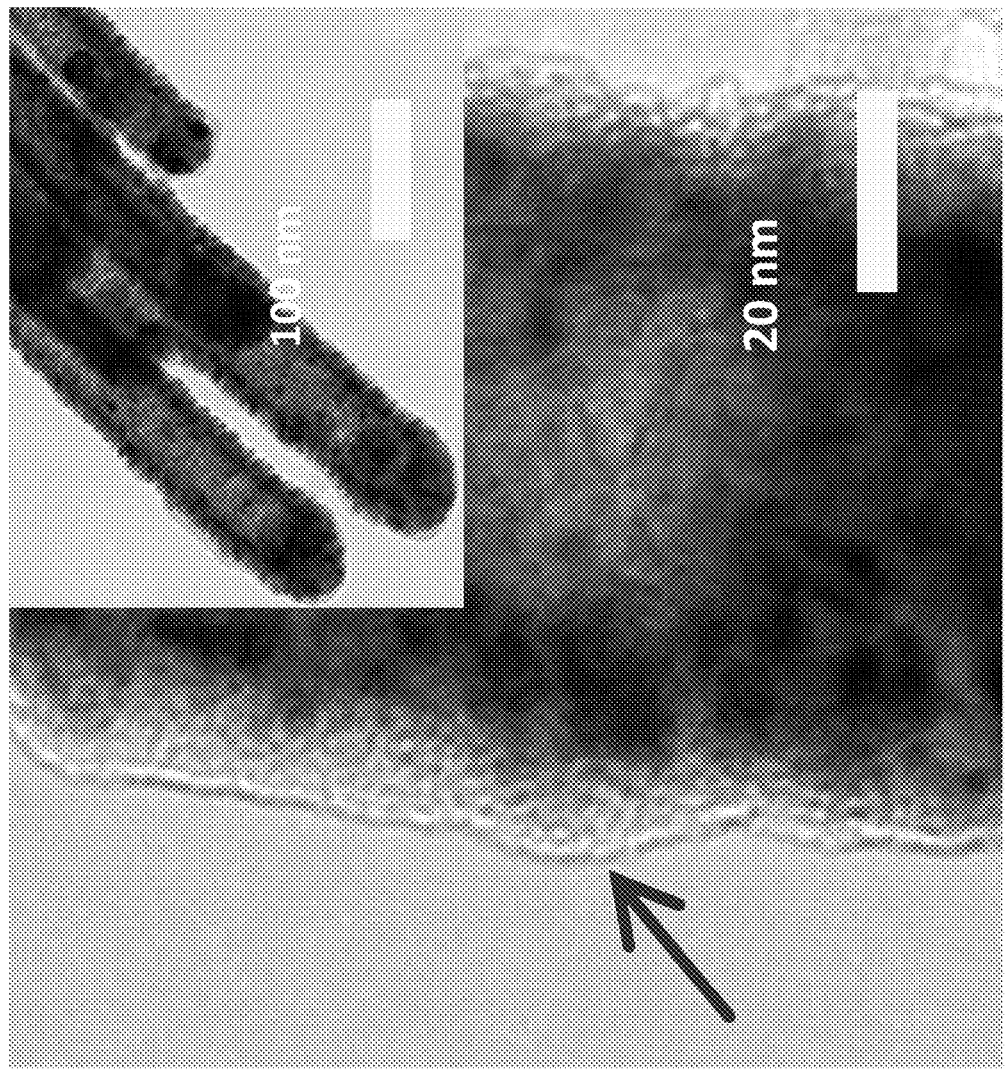

MCNTs were prepared for molecular extraction experiments. Electropolymerization of $_L$-tyrosine using cyclic voltammetry for 30 cycles was performed, as seen in FIG. 1B. The analysis by integrating charge (Q) produced in each cycle revealed that Q decreased over time, indicating a self-limited growth of poly-$_L$-tyrosine (FIG. 1C). This is similar to an electropolymerized non-conducting polymer of phenol and its derivatives that are desirable to produce an ultra-thin film on conducting electrodes (30, 31). Scanning electron microscope (SEM) image showed that Ni was preferentially deposited along the upper parts of the CNTs (FIG. 1D), which resulted from the vertical alignment of the CNTs and the intrinsically vertical deposition of e-beam evaporation. The polymer coating on the CNTs was also characterized with transmission electron microscope (TEM) imaging. The images show a polymeric layer about 10 nm thick on the CNTs (FIG. 1E). The Ni layer was also observed in the TEM images.

Example 2

Figure 1F:
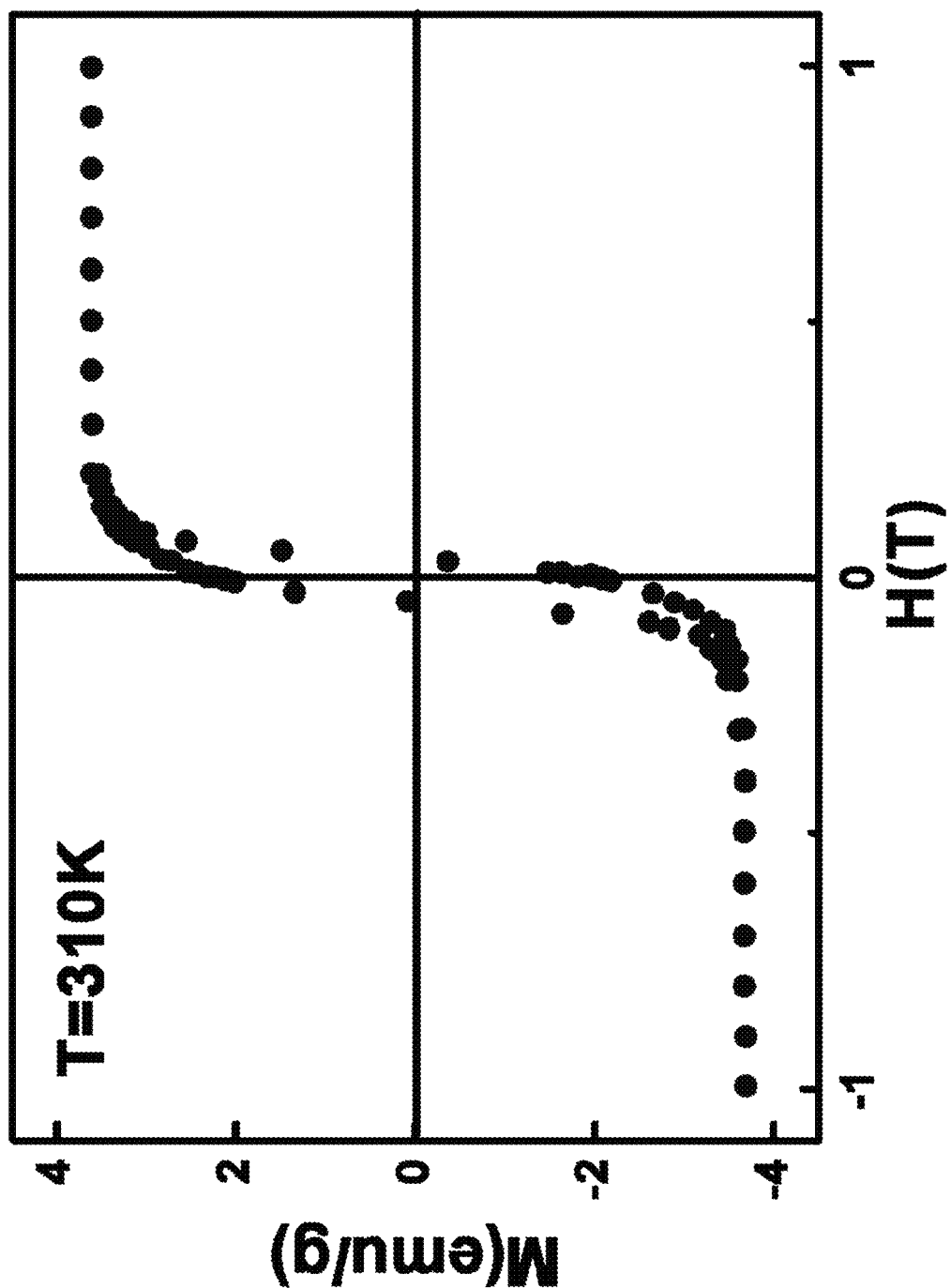
Figure 3:
FIG. 3 illustrates enhanced magnetization of carbon nanotubes (CNTs) by Ni coating. Magnetic attraction reveals an enhanced magnetic drivability of Ni-coated CNTs as compared to as-made CNTs.

The magnetic properties of the MCNTs were evaluated. More specifically, the M-H curve of the MCNTs (such as Ni-coated CNTs) were measured. FIG. 1F shows a saturated magnetization of ~4 emu g$^{-1}$. A minor magnetic hysteresis was also observed, which could be eliminated by replacing Ni with superparamagnetic materials. Meanwhile, the Ni-coated CNTs demonstrated a higher magnetic drivability in comparison with the as-made CNTs (see FIG. 3). After the process, an aqueous suspension of the CNTs with Ni and poly-$_L$-tyrosine modifications was prepared for cell spearing experiments (FIG. 1G).

Figure 4:
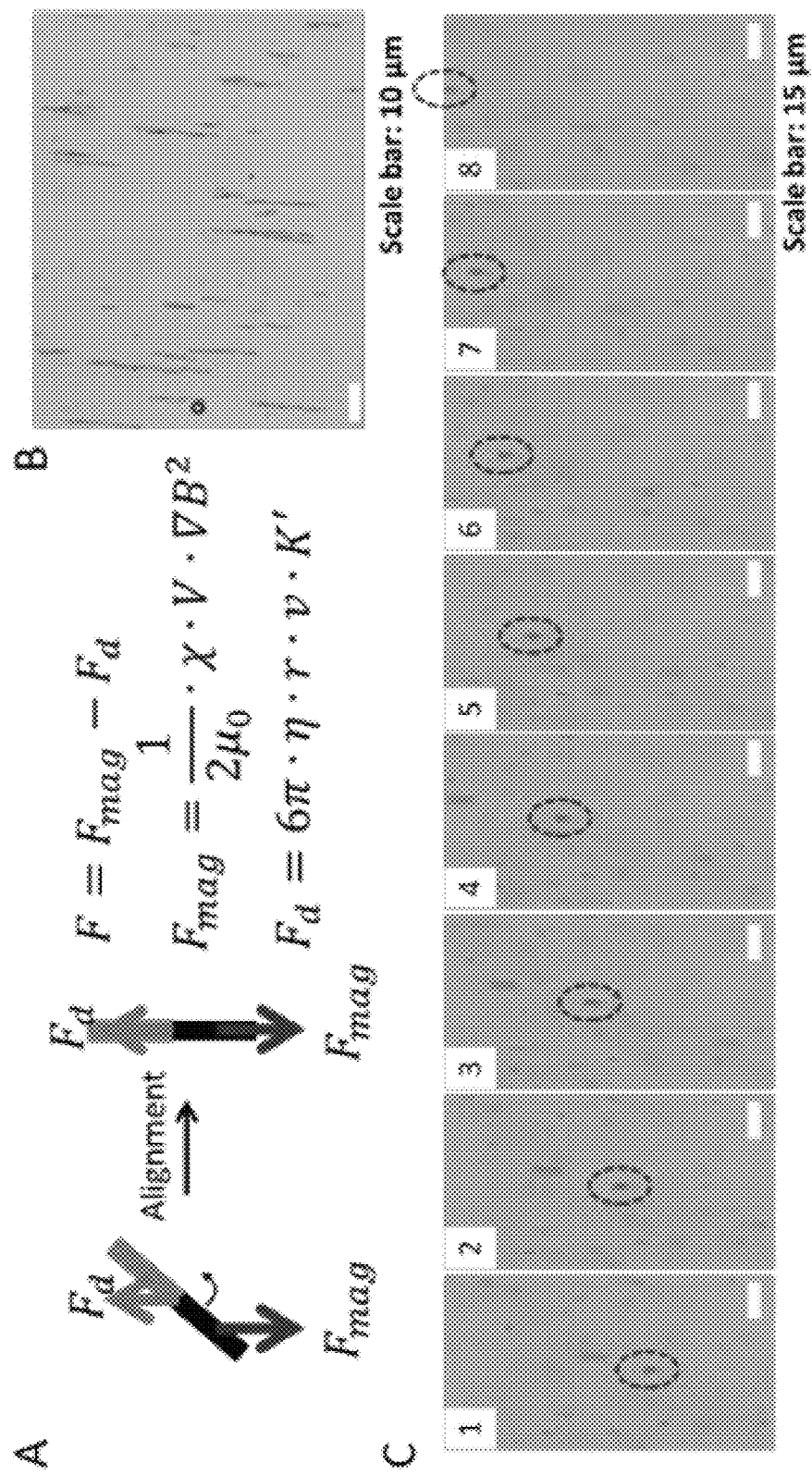
FIG. 4 illustrates a response of MCNTs to magnetic force. (A) Forces analysis of MCNTs in the magnetically guided spearing. The net pulling force (F) on the MCNTs is the summation of the magnetic force ($F_{mag}$) and the drag force ($F_d$) in liquid. In those equations that describe the forces, $\mu_0$ is the magnetic permeability of free space, $\chi$ is the magnetic susceptibility of MCNTs, V is the volume of the nanotube, B is the magnetic field density, $\eta$ is the viscosity of the liquid, r is the radius of the nanotube, v is the velocity of the MCNT in motion, and K' is the shape factor. (B) Microscopy image of MCNTs aligning in magnetic field. (C) Movement of MCNTs by the magnetic force. The images are snapshots over 8 seconds. The numbers index the time. The same MCNT is highlighted with a red circle in each image to show the movement.

As shown in FIG. 4A, the magnetically guided spearing of MCNTs moves under two forces: magnetic force ($F_{mag}$) and drag force ($F_d$). The MCNTs are aligned with their polar axis in the direction of the magnetic gradient due to the unbalanced moments of $F_{mag}$ and $F_d$. When aligned, the net pulling force (F) on MCNTs is the magnetic force ($F_{mag}$) subtracting the drag force ($F_d$) in liquid. Analysis of the forces equations revealed that the thinner the MCNTs (i.e., smaller r) and the larger the magnetic susceptibility (i.e., larger χ), the smaller the $F_d$ and the larger the $F_{mag}$, respectively, and ultimately a net larger pulling F. With a microscope, it was observed that MCNTs tandem attached in alignment to the magnetic field (FIG. 4B). Furthermore, the movement of MCNTs in magnetic field was also evaluated under a microscope. The average speed was approximately 12.7 μm s$^{-1}$ according to their displacements in 8 seconds (FIG. 4C).

Example 3

Figure 5:
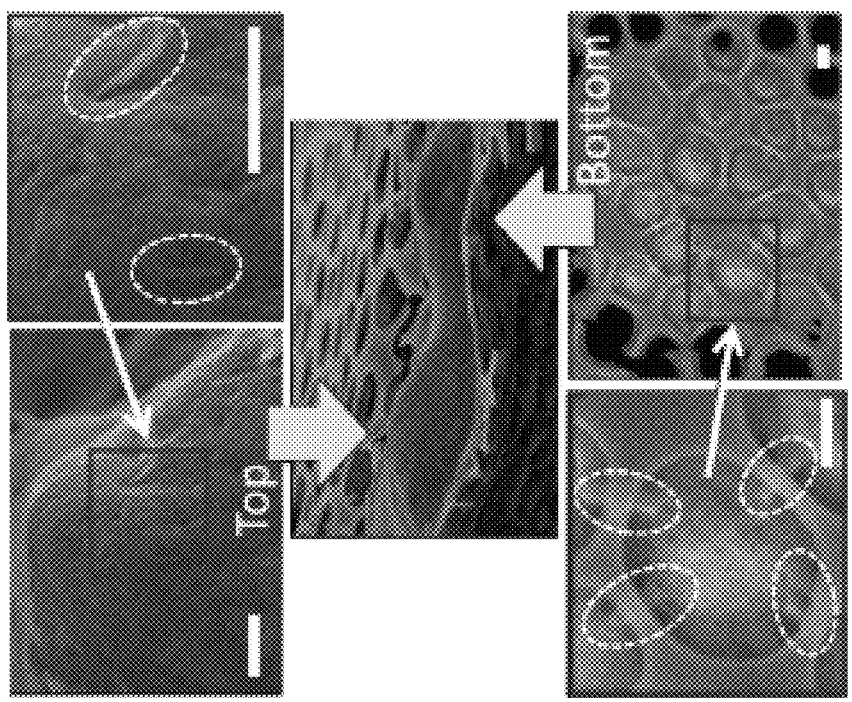
FIG. 5 displays MCNTs spearing into and out of a cell viewed by SEM from top and bottom. Local membrane surfaces in red boxes are magnified. The dashed circles highlight the MCNTs positioned across the cell membrane. Scale bars are 1 µm.

To evaluate the cell penetration by the MCNTs, cells of HEK293, a human embryonic kidney cancer cell line, were first cultured on a carbon-coated TEM sample grid pre-treated with poly-$_L$-lysine. After being speared for 10 min with a rare-earth magnet (0.355 T on the axis and 2 mm above the surface) following the procedure previously described herein, the cells were fixed and dehydrated for SEM inspection. The sample was viewed from both top and bottom to reveal the nanotubes' entry into and exit out of the cells, respectively. The MCNTs were observed in both views (FIG. 5). However, SEM images show the MCNTs in the membrane. MCNTs inside the cell and those that have escaped out of the cells are not visualized. MCNTs were aligned to the magnetic pulling force. Without limitation by any theory, a near-perpendicular entry mode for the MCNTs is dominant at both their entry into and exit out of the cells. Further, without limitation by any theory, the near-parallel adhering that appeared in the SEM images may be caused by the surface tension resulting from the drying process in the preparation of SEM samples. Further, MCNTs in the bottom view had partially speared out of the cell but were held by the carbon film of the TEM grid. With a culture substrate that has a larger opening, the MCNTs would exit out of the cell completely. In comparison with the top view, there were more fibrous structures showing in the bottom. Such fibrous structures have dimensions similar to those of the original MCNTs, indicating an abundant host of MCNTs by cell. According to the morphology of the speared cells (middle image of FIG. 5), the cells remained attached and spread (e.g., stretched on the surface they are attached to). This suggests the integrity of cell membrane and cytoskeleton are maintained, wherein usually they are lost in cells committing apoptosis or necrosis.

Example 4

Figure 6:
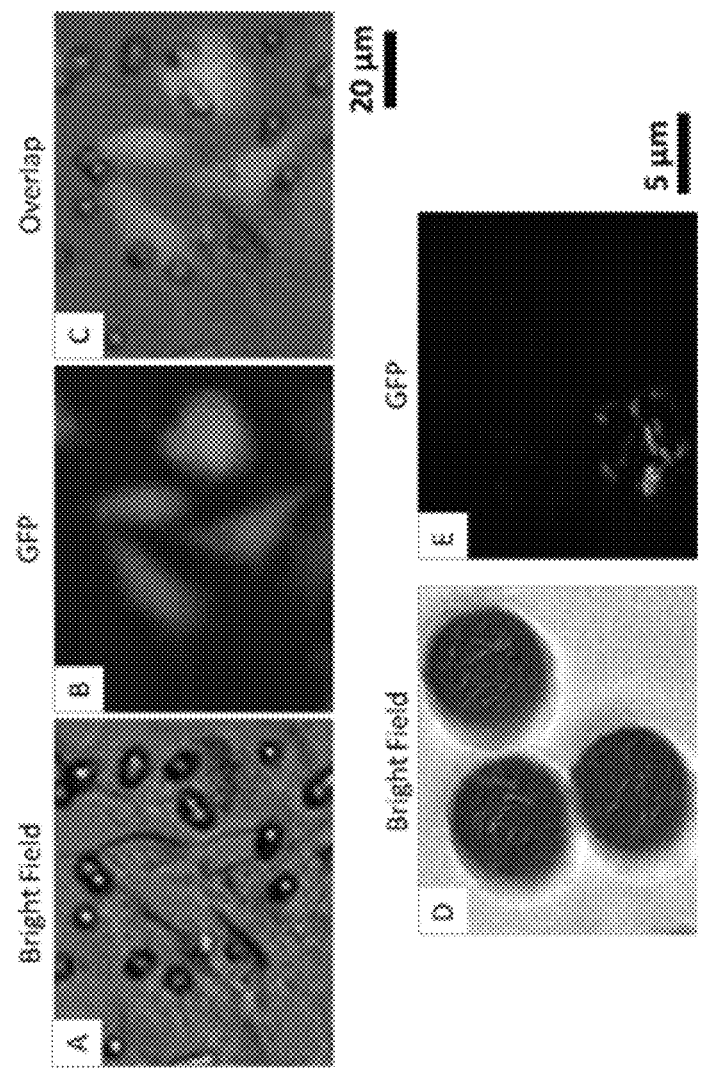
FIG. 6 illustrates the extraction of intracellular GFP by MCNTs spearing. (A-C) Bright-field, dark-field, and overlapped images of GFP-transfected HEK293 cells on a polycarbonate filter, respectively. (D,E) Bright- and dark-field images of MCNTs speared through cells and collected in the pores of a polycarbonate filter, respectively; the appearance of green fluorescence on MCNTs indicates that intracellular GFP was carried out by MCNTs speared through the cells.
Figure 7:
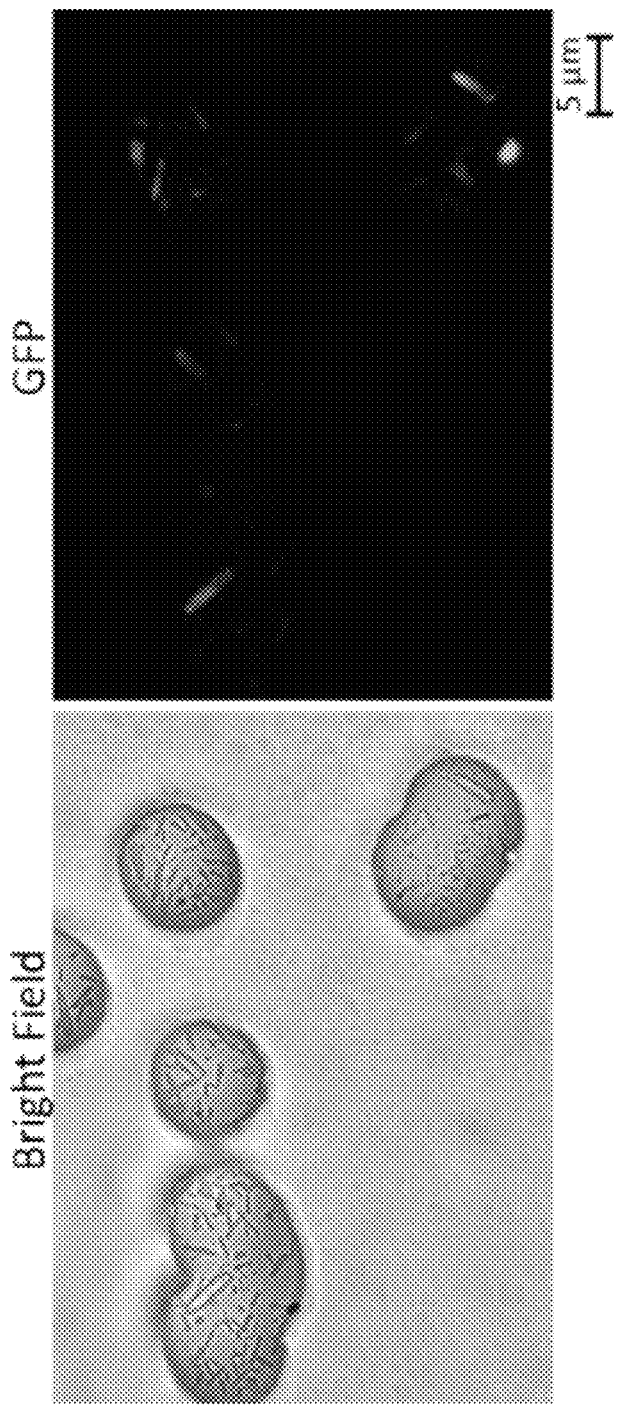
FIG. 7 illustrates intracellular extraction by spearing of GFP-expressed cells with differently sized MCNTs. In comparison of MCNTs trapped within the same pore, larger MCNTs exhibited higher intensities of green fluorescence, indicating higher efficiency of GFP extraction.

To demonstrate the molecular extraction from single cells, a polycarbonate filter with 8 μm (diameter) pores was used as the culture substrate instead of the TEM grid. The pores were able to trap the exited MCNTs from the designated cell and keep them separated from cell to cell. A commercial lipofectamine kit was used to transfect the HEK293 cells at 90% efficiency for GFP overexpression in the cytoplasm. Thus the extraction of intracellular GFP could be indicated by the appearance of GFP on the post-spearing MCNTs. In FIG. 6A-C, the overlay of bright-field and dark-field images of the cell culture showed the alignment and coverage of cells on the pores. Most of the pores were covered by the GFP-HEK293 cells. In FIG. 6D-E, pronounced green fluorescence was observed in the MCNTs speared into a pore. GFP is a soluble protein. GFP could attach to the MCNT in the form of a monolayer. Since the average size of a CNT is 1.5 mm in length and 100 nm in diameter, the maximum loading capacity of the surface is $4\times10^4$ for GFP at the size of 4 nm (length) by 3 nm (diameter). The result shows that MCNTs can carry intracellular molecules out while spearing through cells. MCNTs in some neighboring pores exhibited no fluorescence, suggesting the absence of GFP-HEK293 cells on top of those pores. This evidence confirms the capability of the spearing method to differentiate molecular sampling at single-cell level. The MCNT collection in the pores was not consistent due to the variance of pore size (see FIG. 7). An indexed array for single cell culture may be microfabricated so that the molecular information could be retrieved according to specific index. Also, the numbers, types, sizes, and compositions of the target molecules all have effects on the extracting effectiveness by changing the interactions of MCNTs with cytoplasm and cell membrane. However, their effects could be minimized by magnetically manipulating the MCNTs.

Example 5

Figure 8C:
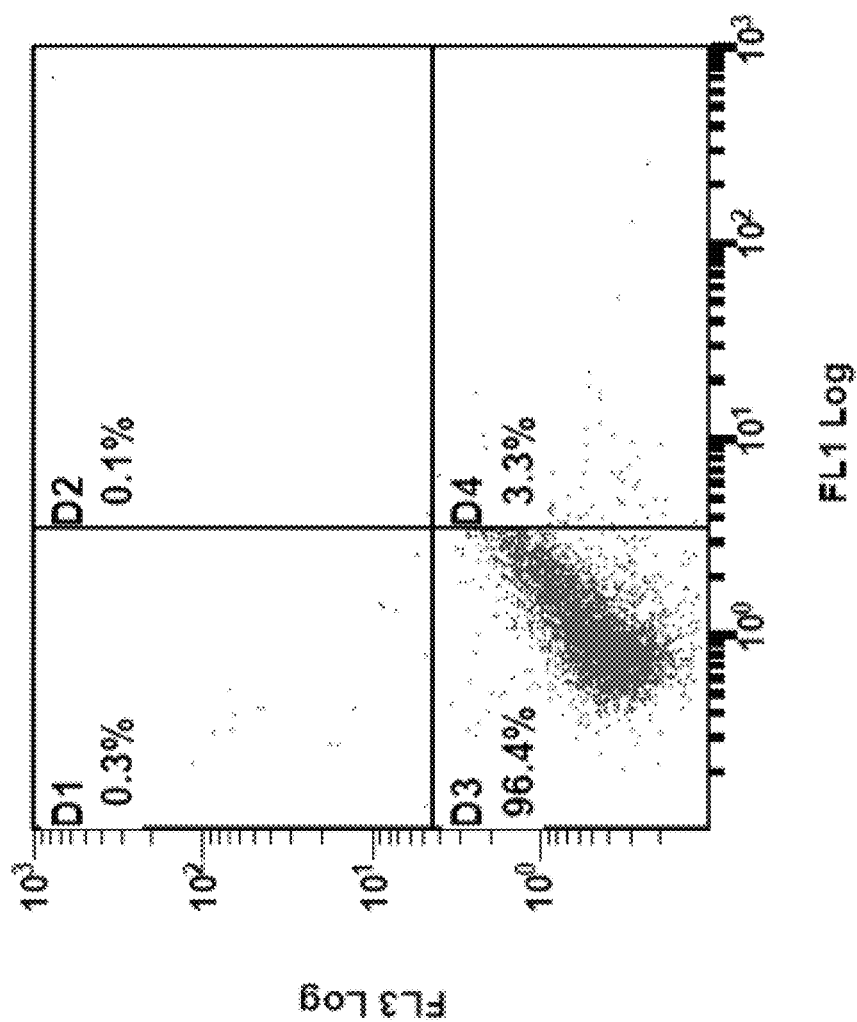
FIG. 8 displays flow cytometry detection of cell viability and apoptosis in MCNTs speared cells. (A) Mag-Only group with normal culture under magnetic field. (B) MCNT-Incubation group with MCNTs but without magnetic field driving. (C) MCNT-Spearing group with MCNTs spearing of cells by magnetic field driving. (D) Cells from group C but left in culture for 12 hours after the spearing. FL1: propidium iodide channel; FL3: Annexin V channel.
Figure 9:
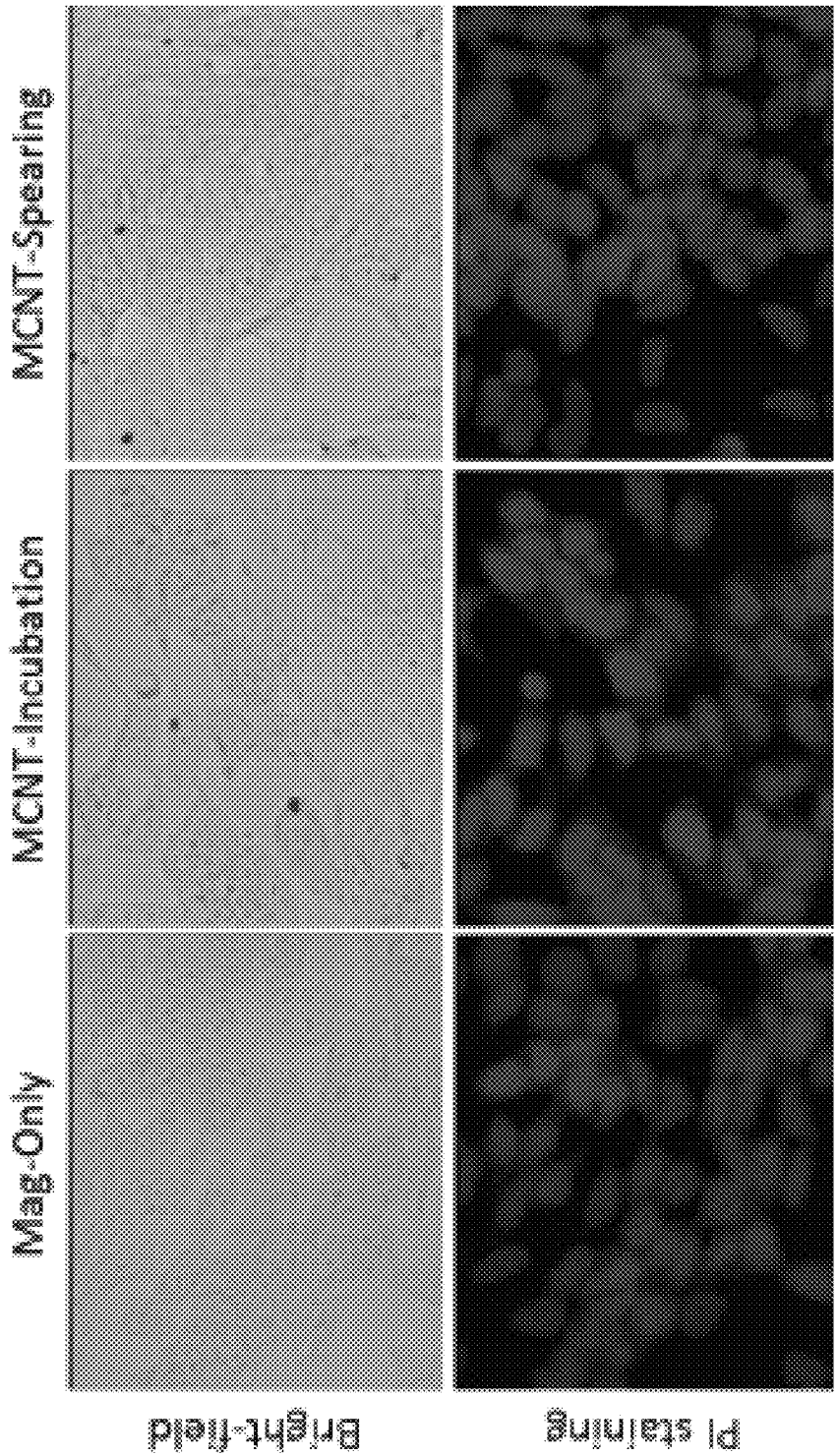
FIG. 9 displays images of cellular morphology. (Top) Bright field images of the cells of the three groups cultured for 24 hours after spearing. Black portions in MCNT-Incubation and MCNT-Spearing groups are solid debris from sample preparation. (Bottom) Nucleus morphology in dark field. All cells were fixed prior to the propidium iodide staining. The horizontal size of the images is 300 mm.

Spearing-mediated molecular extraction may result in is-perturbation of the cells. A systematic study with flow cytometry regarding the cell viability, cell growth, apoptosis, proliferation, cell cycle, and DNA synthesis has shown MCNTs spear a spectrum of cell types without inducing such negative effects (25, 26). However, these previous spearing studies did not include either the process of penetration through cells or the molecular extraction out of the cells. As such some of the key issues such as cell viability, apoptosis and proliferation were reevaluated in three groups of cells: speared (MCNT-Spearing), magnetic field but no MCNTs (Mag-Only), and MCNT incubation but no magnetic field (MCNT-Incubation). An Annexin V-FITC apoptosis detection kit and propidium iodide were used to dual-stain cells for cytometry measurement. As seen in FIG. 8, the cell death and apoptosis were examined in the MCNT-Spearing group and compared to the Mag-Only, MCNT-Incubation, and 12-hours-after-spearing groups. Propidium iodide enters a dying cell through the leakage in its plasma membrane. The spearing led to a slight drop in viability to 96.4% from 98.5% and 98.2% for Mag-Only and MCNT-Incubation, respectively. This indicates an immediate recovery of the membrane after the spearing treatment in most of the cells. With cell culturing for 12 hours, the propidium iodide positive rate returned from 3.3% to 1.4%, which is closer to the level of 1.1% for the Mag-Only control. On the other hand, the Annexin V signal remained stable around 0.5% among all the groups. This indicates that the signal pathways related to programmed cell death are not interrupted by the spearing. The three groups of cells were also compared 24 hours after the treatment. As shown, the morphology of cells in bright field (FIG. 9A-C) exhibited no apparent differences. The nuclei were stained with propidium iodide after fixation. Again, the size and shape of the nucleus did not show apparent differences. Cell density was estimated by nucleus count in randomly chosen fields. For the three groups of cells, the density was 53±3, 51±6, and 52±2 per $mm^2$ (n=5, mean±standard deviation), respectively. It indicated the same proliferation rates among the groups. Together with the results of viability, cell death, apoptosis, and nucleus condition, the spearing method shows the necessary biocompatibility to be applicable to sample intracellular molecules in live cells for the investigation of signal pathways.

Molecular sampling in single live cells was achieved with the successful extraction of intracellular GFP in transfected HEK293 cells. Using a testing model with overexpression of green fluorescent protein (GFP), the nanotubes successfully transported the intracellular GFP out at a single cell level. It was shown that the MCNTs articulated with Ni-coating and poly-$_L$-tyrosine protection can enter into and exit out of the cell across the cell membrane without detectable perturbations to cell viability and proliferation. With all cell conditions maintained post-spearing, the repetitive molecular extraction needed to analyze cellular physiological and pathological signals in a longitudinal fashion may be possible.

While exemplary embodiments of the disclosure have been shown and described, modifications thereof can be made by one skilled in the art without departing from the spirit and teachings of those embodiments. The embodiments described herein are exemplary only, and are not intended to be limiting. Many variations and modifications of the disclosed embodiments are possible and are within the scope of the claimed invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the exemplary embodiments disclosed herein. The disclosures of all patents, patent applications, and publications cited herein are hereby incorporated by reference, to the extent that they provide exemplary, procedural or other details supplementary to those set forth herein.

REFERENCES

1. Khakh B S, North R A (2006) P2X receptors as cell-surface ATP sensors in health and disease. Nature 442(7102):527-532.
2. Chen T, Wu C S, Jimenez E, Zhu Z, Dajac J G, You M, Han D, Zhang X, Tan W (2013) DNA micelle flares for intracellular mRNA imaging and gene therapy. Angew Chem Int Ed 52(7):2012-2016.
3. Khan J, Wei J S, Ringnér M, Saal L H, Ladanyi M, Westermann F, Berthold F, Schwab M, Antonescu C R, Peterson C, Meltzer P S (2001) Classification and diagnostic prediction of cancers using gene expression profiling and artificial neural networks. Nat Medicine 7(6):673-679.
4. Jung T, Schauer U, Heusser C, Neumann C, Rieger C (1993) Detection of intracellular cytokines by flow cytometry. J Immunol Methods 159(1-2):197-207.
5. Buchholz A, Hurlebaus J, Wandrey C, Takors R (2002) Metabolomics: quantification of intracellular metabolite dynamics. Biomol Eng 19(1):5-15.
6. Zhang L, Cui X, Schmitt K, Hubert R, Navidi W, Arnheim N (1992) Whole genome amplification from a single cell: implications for genetic analysis. Proc Natl Acad Sci USA 89(13):5847-5851.
7. Shi Q, Qin L, Wei W, Geng F, Fan R, Shin Y S, Guo D, Hood L, Mischel P S, Heath J R (2012) Single-cell proteomic chip for profiling intracellular signaling pathways in single tumor cells. Proc Natl Acad Sci USA 109(2):419-424.
8. Rubakhin S S, Romanova E V, Nemes P, Sweedler J V (2011) Profiling metabolites and peptides in single cells. Nat Methods 8(4s): S20-S29.
9. Spencer S L, Gaudet S, Albeck J G, Burke J M, Sorger P K (2009) Non-genetic origins of cell-to-cell variability in TRAIL-induced apoptosis. Nature 459(7245):428-432.
10. Haun J B, Devaraj N K, Marinelli B S, Lee H, Weissleder R (2011) Probing intracellular biomarkers and mediators of cell activation using nanosensors and bioorthogonal chemistry. ACS Nano 5(4):3204-3213.
11. Spiller D G, Wood C D, Rand D A, White M R (2010) Measurement of single-cell dynamics. Nature 465(7299):736-745.
12. Wang D, Bodovitz S (2010) Single cell analysis: the new frontier in 'omics'. Trends Biotechnol 28(6):281-290.
13. Joensson H N, Andersson Svahn H (2012) Droplet microfluidics—a tool for single-cell analysis. Angew Chem Int Ed 51(49):12176-12192.
14. Shah P, Zhu X, Chen C, Hu Y, Li C Z (2014) Lab-on-chip device for single cell trapping and analysis. Biomed Microdevices 16(1):35-41.
15. Quinto-Su P A, Lai H H, Yoon H H, Sims C E, Allbritton N L, Venugopalan V (2008) Examination of laser microbeam cell lysis in a PDMS microfluidic channel using time-resolved imaging. Lab Chip 8(3):408-414.
16. Jeffries G D, Edgar J S, Zhao Y, Shelby J P, Fong C, Chiu D T (2007) Using polarization-shaped optical vortex traps for single-cell nanosurgery. Nano Lett 7(2):415-420.
17. Chen X, Kis A, Zettl A, Bertozzi C R (2007) A cell nanoinjector based on carbon nanotubes. Proc Natl Acad Sci USA 104(20):8218-8222.
18. Kim W, Ng J K, Kunitake M E, Conklin B R, Yang P (2007) Interfacing silicon nanowires with mammalian cells. J Am Chem Soc 129(23):7228-7229.
19. Yum K, Na S, Xiang Y, Wang N, Yu M F (2009) Mechanochemical delivery and dynamic tracking of fluorescent quantum dots in the cytoplasm and nucleus of living cells. Nano Lett 9(5):2193-2198.
20. Li H, Sims C E, Wu H Y, Allbritton N L (2001) Spatial control of cellular measurements with the laser micropipet. Anal Chem 73(19):4625-4631.
21. Zhan Y, Sun C, Cao Z, Bao N, Xing J, Lu C (2012) Release of intracellular proteins by electroporation with preserved cell viability. Anal Chem 84(19):8102-8105.
22. Kostarelos K, Lacerda L, Pastorin G, Wu W, Wieckowski S, Luangsivilay J, Godefroy S, Pantarotto D, Briand J P, Muller S, Prato M, Bianco A (2007) Cellular uptake of functionalized carbon nanotubes is independent of functional group and cell type. Nat Nanotechnol 2(2):108-113.
23. Deng Z J, Morton S W, Ben-Akiva E, Dreaden E C, Shopsowitz K E, Hammond P T (2013) Layer-by-layer nanoparticles for systemic codelivery of an anticancer drug and siRNA for potential triple-negative breast cancer treatment. ACS Nano 7(11):9571-9584.
24. Cai D, Mataraza J M, Qin Z H, Huang Z, Huang J, Chiles T C, Carnahan D, Kempa K, Ren Z F (2005) Highly efficient molecular delivery into mammalian cells using carbon nanotube spearing. Nat Methods 2(6):449-454.
25. Cai D, Doughty C A, Potocky T B, Dufort F J, Huang Z P, Blair D, Kempa K, Ren Z F, Chiles T C (2007) Carbon nanotube-mediated delivery of nucleic acids does not result in non-specific activation of B lymphocytes. Nanotechnology 18(36):365101.
26. Cai D, Blair D, Dufort F J, Gumina M R, Huang Z, Hong G, Wagner D, Canahan D, Kempa K, Ren Z F, Chiles T C (2008) Interaction between carbon nanotubes and mammalian cells: characterization by flow cytometry and application. Nanotechnology 19(34): 1-10.
27. Ren Z F, Huang Z P, Xu J W, Wang J H, Bush P, Siegal M P, Provencio P N (1998) Synthesis of large arrays of well-aligned carbon nanotubes on glass. Science 282(5391): 1105-1107.
28. Marx K A, Zhou T, Long D (2005) Electropolymerized films formed from the amphiphilic decyl esters of D- and L-tyrosine compared to L-tyrosine using the electrochemical quartz crystal microbalance. Biomacromolecules 6(3):1698-1706.
29. Marx K A, Zhou T, McIntosh D, Braunhut S J (2009) Electropolymerized tyrosine-based thin films: selective cell binding via peptide recognition to novel electropolymerized biomimetic tyrosine RGDY films. Anal Biochem 384(1):86-95.
30. Chen X, Matsumoto N, Hu Y, Wilson G S (2002) Electrochemically mediated electrodeposition/electropolymerization to yield a glucose microbiosensor with improved characteristics. Anal Chem 74(2):368-372.
31. Yuqing M, Jianrong C, Xiaohua W (2004) Using electropolymerized non-conducting polymers to develop enzyme amperometric biosensors. Trends Biotechnol 22(5): 227-231.
32. Yi X, Shi X, Gao H (2014) A universal law for cell uptake of one-dimensional nanomaterials. Nano Lett 14(2): 1049-1055.

What is claimed is:

1. A method of extracting biomolecules from live cells comprising:
    introducing a plurality of magnetized carbon nanotubes (MCNTs) into a live cell, wherein the MCNTs penetrate the cell membrane under a magnetic force;
    spearing the MCNTs through the cell under the magnetic force, wherein a biomolecule attaches to the MCNTs to form a biomolecule loaded MCNT;
    removing the biomolecule loaded MCNTs from the cell under the magnetic force; and
    collecting the biomolecule loaded MCNTs.

2. The method of claim 1, wherein the live cell retains integrity of the cell membrane and cytoskeleton.

3. The method of claim 1, wherein the viability of the live cells is decreased by less than about 5% when compared to live cells under similar conditions lacking the MCNTs.

4. The method of claim 1, wherein biomolecules are extracted from the same single live cell at different points in time.

5. The method of claim 1, wherein the MCNTs comprises carbon nanotubes, a magnetic metal and an outer polymeric layer.

6. The method of claim 5, wherein the magnetic metal comprises magnetic particles and a magnetic metal layer.

7. The method of claim 5, wherein the outer polymeric layer comprises poly-L-tyrosine.

8. The method of claim 5, wherein the outer polymeric layer is hydrophilic.

9. The method of claim 5, wherein the outer polymeric layer is biocompatible.

10. The method of claim 1, wherein the biomolecules comprise intracellular molecules, intracellular proteins, analytes, signaling molecules, or combinations thereof.

11. The method of claim 1 further comprising employing the collected biomolecule loaded MCNTs for cellular signaling analysis.

12. A method of preparing magnetized carbon nanotubes (MCNTs) comprising:

growing carbon nanotubes;

coating the carbon nanotubes with a magnetic metal to yield MCNTs, wherein the magnetic metal comprises nickel; and coating the MCNTs with an outer polymeric layer, wherein the outer polymeric layer is hydrophilic and biocompatible.

13. A method of extracting biomolecules from live cells comprising:

introducing a plurality of magnetized nanostructures (mNSs) into a bioentity, wherein the mNSs penetrate a cell membrane of the bioentity under a magnetic force;

spearing the mNSs through the bioentity under the magnetic force, wherein biomolecules attach to the mNS to form a biomolecule loaded mNSs;

removing the biomolecule loaded mNSs from the bioentity under the magnetic force; and collecting the biomolecule loaded mNSs.

14. The method of claim 13, wherein the bioentity retains integrity of the cell membrane and cytoskeleton, and wherein the bioentity comprises a single cell, a clump of cells, a piece of live tissue, or combinations thereof.

15. The method of claim 13, wherein biomolecules are extracted from the same bioentity at different points in time.

* * * * *